(12) United States Patent
Wisotzky et al.

(10) Patent No.: US 11,547,290 B2
(45) Date of Patent: Jan. 10, 2023

(54) MEDICAL IMAGING DEVICE, METHOD, AND USE

(71) Applicant: Fraunhofer-Gesellschaft zur Förderung der angewandten Forschung e.V., Munich (DE)

(72) Inventors: Eric Wisotzky, Berlin (DE); Peter Eisert, Berlin (DE); Anna Hilsmann, Berlin (DE)

(73) Assignee: Fraunhofer-Gesellschaft zur Förderung der angewandten Forschung e.V., Munich (DE)

( * ) Notice: Subject to any disclaimer, the term of this patent is extended or adjusted under 35 U.S.C. 154(b) by 0 days.

(21) Appl. No.: 16/949,751

(22) Filed: Nov. 12, 2020

(65) Prior Publication Data
US 2021/0137375 A1     May 13, 2021

(30) Foreign Application Priority Data
Nov. 13, 2019 (DE) ..................... 10 2019 217 541.4

(51) Int. Cl.
*A61B 1/227* (2006.01)
*H04N 5/225* (2006.01)
(Continued)

(52) U.S. Cl.
CPC ............ *A61B 1/227* (2013.01); *A61B 1/0005* (2013.01); *A61B 1/0638* (2013.01); *A61B 90/20* (2016.02);
(Continued)

(58) Field of Classification Search
CPC ..... A61B 1/227; A61B 1/0005; A61B 1/0638; A61B 90/20; H04N 5/2256; H04N 2005/2255; H04N 5/265
See application file for complete search history.

(56) References Cited

U.S. PATENT DOCUMENTS

| 8,965,474 B2* | 2/2015 | Yamaguchi ............ A61B 1/063 600/323 |
| 2011/0295062 A1* | 12/2011 | Gratacos .......... A61B 1/000094 600/109 |

(Continued)

FOREIGN PATENT DOCUMENTS

| JP | 2011010998 A | 1/2011 |
| JP | 2011224038 A | 11/2011 |

(Continued)

OTHER PUBLICATIONS

"Japanese Application Serial No. 2020-189620, Office Action dated Jun. 21, 2022", w/English Translation, (dated Jun. 21, 2022), 7 pgs.

(Continued)

*Primary Examiner* — Richard A Hansell, Jr.
(74) *Attorney, Agent, or Firm* — Schwegman Lundberg & Woessner, P.A.

(57) ABSTRACT

A medical imaging device, comprising a illumination unit, can be configured to illuminate a tissue area with light from a first spectral range, comprising a range of visible wavelengths, and with light from a second spectral range, which is different from the first spectral range, an imaging unit, configured to detect light from the first spectral range and to generate a first image of the tissue area on the basis of the detected light from the first spectral range and furthermore configured to detect light from the second spectral range and to generate a second image of the tissue area on the basis of the detected light from the second spectral range, and a superposition unit, configured to generate a superimposed image on the basis of the first and second image in such a way that, in the superimposed image, on the basis of a visual highlighting, it is possible to identify whether and where the tissue area comprises highlight regions which are characterized by an increased emission of light from the second spectral range in comparison to other regions of the tissue (Continued)

area. The document furthermore relates to a method for image-based support for a medical intervention, and to a use of an imaging device in such a method.

14 Claims, 3 Drawing Sheets

(51) Int. Cl.
*A61B 1/06* (2006.01)
*A61B 90/20* (2016.01)
*A61B 1/00* (2006.01)

(52) U.S. Cl.
CPC ... *H04N 5/2256* (2013.01); *H04N 2005/2255* (2013.01)

(56) References Cited

U.S. PATENT DOCUMENTS

| | | | | |
|---|---|---|---|---|
| 2012/0083772 | A1* | 4/2012 | Rubinfeld | A61K 38/44 606/4 |
| 2012/0220823 | A1 | 8/2012 | Choe et al. | |
| 2013/0012794 | A1* | 1/2013 | Zeng | G01J 3/28 600/179 |
| 2015/0257635 | A1* | 9/2015 | Kubo | A61B 1/0655 600/109 |
| 2015/0351637 | A1* | 12/2015 | Ruppersberg | A61B 1/07 600/474 |
| 2016/0026908 | A1* | 1/2016 | van der Merwe | G07F 7/1008 235/494 |
| 2017/0049310 | A1* | 2/2017 | Lepple-Wienhues | A61B 1/00057 |
| 2017/0071509 | A1* | 3/2017 | Pandey | A61B 1/00045 |
| 2018/0218714 | A1* | 8/2018 | Yamaguchi | G06T 3/0006 |
| 2021/0307687 | A1* | 10/2021 | Culman | A61B 90/361 |

FOREIGN PATENT DOCUMENTS

| | | |
|---|---|---|
| JP | 2012511361 A | 5/2012 |
| WO | WO-2017221335 A1 | 12/2017 |
| WO | WO-2018045269 A1 | 3/2018 |

OTHER PUBLICATIONS

"Japanese Application Serial No. 2020-189620, Office Action dated Oct. 29, 2021", w/English Translation, (dated Oct. 29, 2021), 9 pgs.

\* cited by examiner

MEDICAL IMAGING DEVICE, METHOD, AND USE

CLAIM FOR PRIORITY

This application claims the benefit of priority of German Application No. 10 2019 217 541.4, filed Nov. 13, 2019, which is hereby incorporated by reference in its entirety.

TECHNICAL FIELD

This document relates to a medical imaging device, to a method for providing image-based support for a medical intervention, and to a use of such an imaging device in such a method.

BACKGROUND

During medical interventions or examinations, it is often necessary to distinguish between different types of tissue within a single tissue area. For example, it may be necessary to distinguish between defectively altered or proliferating tissue (abnormal tissue) and surrounding, healthy tissue of the tissue area. Based on such a distinction, medical staff, for example, are able to make a diagnosis and/or decide on a site for application of a local therapy, for example an injection or excision of the abnormal tissue. The abnormal tissue may be, for example, tumor tissue, cyst tissue and/or an expanding tissue growth, for example cholesteatoma tissue, i.e. an inflammatory expanding tissue growth in a middle-ear tissue area.

SUMMARY/OVERVIEW

Medical imaging devices by means of which images of a tissue area may be produced may be consulted in order to distinguish between different types of tissue within the tissue area. Here, the problem may arise that the different types of tissue are not always visually clearly distinguishable. For example, cholesteatoma tissue is not easily visually distinguishable from surrounding middle ear tissue, in particular bone tissue. In particular, this hinders complete excision of the abnormal tissue, something which is indispensable for successful therapy.

The proposed imaging device can allow an improved distinction of various types of tissue within a tissue area. Furthermore, a method for image-based support for a medical intervention and a use of the proposed imaging device in the proposed method are provided.

A medical imaging device in an example comprises
  an illumination unit, configured to illuminate a tissue area with light from a first spectral range, comprising a range of visible wavelengths, and with light from a second spectral range, which is different from the first spectral range,
  an imaging unit, configured to detect light from the first spectral range and to generate a first image of the tissue area on the basis of the detected light from the first spectral range and furthermore configured to detect light from the second spectral range and to generate a second image of the tissue area on the basis of the detected light from the second spectral range,
  a superposition unit, configured to generate a superimposed image on the basis of the first and second image in such a way that, in the superimposed image, on the basis of a visual highlighting, it is possible to identify whether and where the tissue area comprises highlight regions which are characterized by an increased emission of light from the second spectral range in comparison to other regions of the tissue area.

With the imaging device according to the present approach, by the generation of images (specifically the first and second image), different types of tissue within the tissue area may be clearly distinguished from one another on the basis of the detected light from different spectral ranges (specifically from the first and second spectral range) in conjunction with the visual highlighting in the superimposed image.

In particular, this concerns types of tissue that differ from one another with regard to the spectral properties within the first and/or second spectral range, in particular the second spectral range. The increased emission of light from the second spectral range in the highlight regions in comparison to the other regions of the tissue area may occur on account of increased reflection and/or scattering and/or remission and/or other emission of light from the second spectral range in comparison to the other regions of the tissue area.

The superimposed image produced by means of the superposition unit, at the same time, serves advantageously as an overview of the tissue area, on the basis of which various features of the tissue area which result in particular from the first image may be identified, and also serves to make use of additional information contained in the second image as a result of the visual highlighting, such that it is possible to identify whether and where the tissue area comprises highlight regions. The information thus provided may enable or simplify diagnoses and/or and therapeutic decisions.

In this application, "highlight regions" include both the aforementioned regions of the tissue area with increased emission of light from the second spectral range in comparison to other regions of the tissue area, as well as the regions of an image corresponding to these tissue regions, in particular the regions of the superimposed image characterized by means of the visual highlighting.

The term "visible wavelengths" is understood to mean wavelengths of visible light, that is to say wavelengths approximately between 380 nm and 750 nm, in particular between 400 nm and 700 nm. The first spectral range and/or the second spectral range may include a single continuous interval of wavelengths or a plurality of intervals of wavelengths.

The second spectral range may be contained wholly or partially in the first spectral range, may overlap the first spectral range in part, or may be disjoint from the first spectral range, that is to say has no overlap therewith. The second spectral range may preferably have a lower bandwidth than the first spectral range. The first and/or second spectral range may also comprise wavelengths outside visible light, in particular wavelengths in the near-ultraviolet range and/or in the near-infrared range. The first spectral range may comprise, for example, all visible wavelengths, inclusive or exclusive of the second spectral range, or a sub-range of the visible wavelengths, inclusive or exclusive of the second spectral range.

The first image and/or the second image and/or the superimposed image may be an optical image, that is to say a real or virtual image generated or generatable by means of an optical imaging process, a display image, that is to say an image presented or presentable on a display, screen or another display unit, or an image dataset, that is to say a digital dataset detected or detectable by means of a detection unit and corresponding to an optical image and/or a display image.

By means of a continuous and/or repeated generation of the first and/or second image and/or of the superimposed image, a change to the tissue area, for example a change on account of a performed excision or other therapeutic measures, may be monitored, for example during a medical intervention, and may be analyzed for further therapeutic and/or diagnostic steps.

The first spectral range may comprise at least one sub-range of visible wavelengths greater than 450 nm and/or omit a sub-range of wavelengths less than 450 nm, in particular at least one sub-range of the second spectral range. The second spectral range may include at least one sub-range of wavelengths between 350 nm and 500 nm, in particular between 370 nm and 480 nm, preferably between 400 nm and 450 nm, and may omit at least one sub-range of wavelengths smaller than 380 nm and/or greater than 450 nm.

For example, the second spectral range may consist of a single interval with a lower limit between 350 nm and 420 nm and an upper limit between 430 nm and 500 nm.

With the spectral ranges thus selected, the imaging device is particularly well suited for examining a tissue area in which abnormal tissue is characterized by an increased emission of light within the aforesaid ranges (350 nm to 500 nm, that is to say approximately near-ultraviolet to blue-green), since such abnormal tissue is then identifiable in the superimposed image on the basis of the visual highlighting. For example, in this way, it is possible to make use of the fact that cholesteatoma tissue has an increased reflection and reduced absorption of light with wavelengths from 370 nm to 480 nm in comparison to surrounding bone tissue in the middle ear. Therefore, the visual highlighting in this case may facilitate the identification (and thus also decisions regarding the removal) of cholesteatoma tissue by medical staff.

The omission of a sub-range of wavelengths smaller than 380 nm may reduce or avoid damage to the tissue area caused by ultraviolet light. The omission of a sub-range of wavelengths greater than 450 nm enables a good spectral separation of the first and second spectral range.

A spectral range omitting/not overlapping a wavelength range means, throughout this application, that said spectral range essentially omits/does not overlap said wavelength range. In particular, when generating/detecting light of said spectral range using a physical separation (e. g., by means of an optical filter and/or an emission band of the illumination unit and/or a detection band of the imaging unit), a certain fraction of the omitted/not overlapping wavelength range may still be generated/detected. Said fraction may be, for example, less than 10%, in particular less than 1%, preferably less than 0.1% of the light which is generated/detected overall.

The first and/or second spectral range may also be selected differently, such that the imaging device is particularly suitable for distinguishing other types of tissues. For example, the second spectral range may include wavelengths in an interval around a central wavelength of 490 nm and/or in an interval around a central wavelength of 640 nm and may omit at least sub-ranges of wavelengths outside the respective intervals, wherein the intervals may be given by suitable bandwidth, for example bandwidth between 10 nm and 100 nm around the respective central wavelengths. The imaging device is therefore well suited, for example, for examining nerve tissue; for example, parotid tissue and nerve tissue have an increased reflection and reduced absorption at wavelengths of approximately 490 nm and approximately 640 nm in comparison to surrounding tissue.

In order to allow the generation of the first image and of the second image, the imaging device may be configured to allow a separate detection of light from the first spectral range and of light from the second spectral range. This may be achieved in different ways, for example by spatially separate and/or temporally separate detection of light from the first spectral range and light from the second spectral range in accordance with the possibilities described hereinafter.

The illumination unit may be configured for sequential illumination of the tissue area with light from the first and second spectral range, for example such that the tissue area is first illuminated with light from the first spectral range and is then illuminated with light from the second spectral range. Since the temporal sequence of the illumination with light from the first and second spectral range is known, a temporally separate detection of light from the first spectral range and of light from the second spectral range is thus possible. By sequential illumination of the tissue area with light from the first and second spectral range, it may be ensured, in particular, that spectral properties of the tissue area in the second spectral range are detectable separately, i.e. without simultaneous illumination of the tissue area with light from the first spectral range.

For sequential illumination, the illumination units may comprise, for example, a broadband light source, for example a halogen-metal halide lamp or a broadband LED light source, in each case configured to simultaneously emit light both from the first and from the second spectral range. Furthermore, the illumination unit may have a filter unit that is able to be switched over between transmission of the first and second spectral range.

The illumination unit, however, may also comprise a plurality of light sources, for example LED light sources and/or laser light sources, which are able to be switched over and/or combined for the sequential generation of light from the first and second spectral range.

The illumination unit may be configured for the simultaneous illumination of the tissue area with light from the first and second spectral range. The simultaneous illumination of the tissue area allows a particularly simple design of the illumination unit, for example with use of a broadband light source as described above, although in this case there is no need for a switchable filter unit.

The imaging unit may be configured for the sequential generation of the first and second image. A particularly simple design of the imaging unit is thus possible, and the imaging unit in this case, for example, may have a single beam path and a single broadband detector for generation of the first and second image.

In particular, it may be provided that the imaging unit is configured for the sequential generation of the first and second image, and the illumination unit is configured for the sequential illumination of the tissue area with light of the first and second spectral range. To this end, for example, an alternating insertion and/or removal of one or more optical filters of the illumination unit and/or a switching of light sources of the illumination unit may be synchronized with a detection of a series of images, so that, within the series of images, the first and second image or the first and second series of images alternate.

It may also be provided that the imaging unit is configured for the sequential generation of the first and second image, and the illumination unit is configured for the sequential illumination of the tissue area with light of the first and second spectral range. To this end, for example, an alternating insertion and/or removal of one or more optical filters of the imaging unit may be synchronized with a detection of a series of images, so that, within the series of images, the first and second image alternate.

The imaging unit may be configured for the simultaneous generation of the first and second image, wherein the first and second image are spatially separated by means of at least one optical filter, that is to say light from the first spectral range and light from the second spectral range are detectable spatially separately. By means of the simultaneous generation of the first and second image, a particularly high time resolution is possible, for example.

It may also be provided, for example, that the imaging unit is configured for the simultaneous generation of the first and second image, and the illumination unit is configured for the simultaneous illumination of the tissue area with light of the first and second spectral range. To this end, for example, a broadband light generated by means of broadband illumination and emitted by the tissue area may be separated spatially by means of a dichroic mirror into two components, corresponding to the first and second spectral range, and may be detected by means of separate sensors or spatially separate regions of a single sensor.

By means of a suitable selection and combination of the different mentioned possibilities for sequential and/or simultaneous illumination and/or detection, the various advantages may be combined with one another and optimized in respect of a desired application.

The medical imaging device may be or may comprise an ear-nose-throat (ENT) microscope and/or an operating microscope (surgical microscope), in particular a surgical microscope for the ENT area, and/or an endoscope, whereby it is particularly suitable for use in medical procedures that are performed with use of such instruments.

The imaging unit may have at least one objective lens for detecting light from the first and second spectral range. The imaging unit and/or the superposition unit may comprise at least one eyepiece for visually displaying the first image and/or the second image and/or the superimposed image.

The medical imaging device may comprise a detection unit which is configured to detect a first pixel dataset, corresponding to the first image and/or the first series of images, and a second pixel dataset, corresponding to the second image and/or the second series of images.

The first and second image are provided in the form of a digital image dataset, specifically in the form of the first and second pixel dataset, by means of the detection unit, which allows for flexible further processing, storage and/or display.

Such a detection unit may comprise, in particular, at least one image sensor (in the case of sequential detection of the first and second image, preferably at least two image sensors), for example a CCD or CMOS chip, which is configured for spatially resolved detection of the first and/or second pixel dataset.

The superposition unit may be or may comprise an image processing unit which is configured to generate a third pixel dataset, corresponding to the superimposed image and/or the superimposed series of images, on the basis of the first and second pixel dataset.

The detection unit may be configured for the repeated detection of images with a repetition frequency of at least 30 Hz, preferably at least 60 Hz. The image processing unit may be configured to generate the third pixel dataset with a latency of less than 100 ms, preferably less than 50 ms.

Due to the time resolution thus attainable and short temporal delay between the generation of the first and second image and the generation of the superimposed image, a display of the superimposed image in real time is made possible, whereby in particular a surgical intervention at the tissue area may be performed with direct visual feedback.

The imaging device may be configured to show and/or display the superimposed image by means of one or more displays and/or by means of one or more eyepieces.

The use of eyepieces may allow a user intuitive and close access to the superimposed image. The use of a display may allow a number of people to view the superimposed image simultaneously, and also offers particularly flexible display options, by means of which, for example, the visual highlighting may be seen particularly clearly.

The superposition unit may be configured to generate the superimposed image by superimposing the first and second image, in particular optically or digitally.

An optical superposition is a particularly simple possibility for generating the superimposed image and is possible, in particular, if the highlight regions in the second image are clear and the first image is not too light in comparison to the second image. In order to ensure this, it may also be possible to soften the first image by means of a gray filter and/or to suitably adapt an illumination level of the illumination with light from the first and/or second spectral range.

In the case of a digital superposition, an intensification and/or softening of the first and/or second image may be achieved in a simple manner by linear or non-linear scaling of the first and/or second pixel dataset.

The superposition unit may be configured to generate the superimposed image by alternate generation and/or display and/or hiding and/or refreshing of the first and second image.

The frequency of the alternation between the first and second image and/or the refreshing of the first or second image may be at least 30 Hz, preferably at least 60 Hz.

By means of the time resolution thus attainable, a display of the superimposed image in real time may again be made possible, whereby in particular a surgical intervention at the tissue area may be performed with direct visual feedback.

The image processing unit may be configured to generate a highlight image on the basis of the second image or on the basis of the first and second image, which highlight image comprises the visual highlighting. The superposition unit may then be configured to generate the superimposed image by superimposing the first image with the highlight image. The superimposed image may also be generatable by replacing regions of the first image by the highlight image or by corresponding regions of the highlight image.

The image processing unit may be configured to generate the visual highlighting and/or the highlight image by means of a threshold value for the second image and/or by means of a segmentation of the second image and/or by means of a color space transformation and/or a feature extraction and/or an object classification and/or a machine learning algorithm and/or a neural network.

In this way, the visual highlighting and/or the highlight image may be determined robustly and/or may be displayed in a clearly visible manner.

The image processing unit may be configured to select a type of visual highlighting on the basis of a user input. The visual highlighting may thus be adjustable depending on user preference and/or required information.

The visual highlighting may comprise a color-based delimitation and/or an edging of the highlight regions and/or marking of the highlight regions by means of at least one symbol and/or lettering. The visual highlighting may comprise a display of a quantitative feature of the first and/or second image, for example by means of a color assignment table and/or by means of blended numerical values and/or superimposed contour lines. The quantitative feature may be, for example, a quotient or other function of pixel values of the second and/or first image. The visual highlighting may comprise a marking of an absence of highlight regions, for example by means of a symbol and/or lettering introduced into the superimposed image. The visual highlighting may be or may comprise a false color display of the second image.

The superimposed image and/or the first image and/or the second image may be a two-dimensional image or a stereo image, i.e. a three-dimensional image composed of a left and a right component. The imaging unit may be configured to divide light emitted by the tissue area in order to generate a left and a right component of the first and second image.

If the superimposed image is a stereo image, the imaging device may be configured to display the superimposed image by means of two eyepieces and/or to show the superimposed image on a 3D display.

Generation of the superimposed image and/or the first and/or second image as a stereo image is particularly advantageous for use of the medical imaging device in conjunction with a surgical intervention, since spatial perception is made possible as a result of the stereo image. Similar advantages are provided if the visual highlighting is a highlighting in an augmented reality display (AR display).

The detection unit may comprise an image sensor with at least one pixel group, preferably a plurality of pixel groups, wherein each of the pixel groups comprises at least one first pixel, preferably a plurality of first pixels, configured to detect light from the first spectral range, and at least one second pixel, preferably a plurality of second pixels, configured to detect light from the second spectral range. The pixel groups may be arranged in particular in a plurality of rows of a plurality of pixel groups. The pixel groups may be arranged in a coplanar manner, in particular on a joint sensor chip. An optical filter, in particular a bandpass filter, for transmitting the particular spectral range or a sub-range of the particular spectral range may be arranged on each of the pixels.

Light from the first and second spectral range may be detected simultaneously in a particularly simple manner by means of an image sensor comprising pixel groups of the described kind, and a spatially and spectrally resolved image dataset may be generated, which then may be divided by the image processing unit into the first and second pixel dataset.

By appropriate choice of the number of pixels in each pixel group and/or the optical filters arranged on the pixels of each pixel group, a high spectral resolution may be attained, and, at the same time, a high time resolution is attainable by means of the simultaneous detection.

In the case of an image sensor having pixel groups of the kind described above, it may be provided that each pixel group contains at least three pixels, wherein at least two pixels of each pixel group are first pixels as defined above and the remaining pixel or pixels are second pixels as defined above.

The first pixels may be disjoint from the second pixels, i.e., no first pixel is simultaneously a second pixel. One or more, but not all, of the first pixels may simultaneously be second pixels (for instance, in the case of overlapping first and second spectral ranges).

If each of the pixel groups contains a plurality of first pixels and/or a plurality of second pixels, different ones of the first and/or second pixels, respectively, may be configured to detect light from different sub-ranges of the first and/or second spectral range, respectively. In this way, spectrally resolved detection of light from the first and/or second spectral range may be enabled.

The pixels of each pixel group may be arranged in a coplanar manner. The pixels of each pixel group may be arranged in one or more rows of one or more pixels per row. For example, each pixel group may comprise a row of three pixels or three rows of one pixel per row. In this example the image sensor may be a conventional or adapted RGB sensor. In a further example each pixel group may comprise n rows of n pixels per row (with n=1, 2, 3, . . . ).

A particularly high spectral resolution (but with reduced time resolution) may also be attained in another way. For example, the imaging device may be configured for the sequential scanning, line by line, of the tissue area with use of a spectrally resolving detection unit.

This may be implemented, for example, in the following way: The illumination unit may comprise a slit aperture and a tiltable mirror for projecting a slit-shaped illumination onto the tissue area, and the imaging unit may comprise a tiltable mirror for the stationary imaging of a region of the tissue area corresponding to the slit-shaped illumination. The imaging unit may then also comprise a spectrometer unit, for example a prism spectrometer unit or a grating spectrometer unit, which is configured for the spectral fanning out of detected light of the region of the tissue area corresponding to the slit-shaped illumination and for imaging the spectrally fanned-out light onto an image sensor perpendicularly to the longitudinal direction of the slit-shaped illumination. By performing the tilting of the tiltable mirror and the sequential detection of images by means of the image sensor in a temporally coordinated manner, a spatially and spectrally resolved image dataset may then be generated.

The illumination unit and/or the imaging unit may comprise a multi-filter unit, for example a filter wheel, with a plurality of optical filters, wherein, by moving the multi-filter unit, each of the filters may be introduced into a beam path of the illumination unit and/or the imaging unit. By performing the movement of the multi-filter unit and the sequential detection of images by means of the image sensor in a temporally coordinated manner, a spatially and spectrally resolved image dataset may then be generated. A high spectral resolution may be attained in this way as well.

A method according to the present approach for providing image-based support for a medical intervention comprises the following steps:

illuminating a tissue area with light from a first spectral range, comprising a range of visible wavelengths, and with light from a second spectral range, which is different from the first spectral range, detecting light from the first spectral range and from the second spectral range, generating a first image of the tissue area on the basis of the detected light from the first spectral range and a second image of the tissue area on the basis of the detected light from the second spectral range, generating a superimposed image from the first and second image in such a way that, in the superimposed image, on the basis of a visual highlighting, it is possible to identify whether and where the tissue area comprises highlight regions which are characterized by an increased emission of light from the second spectral range in comparison to other regions of the tissue area.

The method, similarly to the proposed imaging device, is characterized in that, by the generation of images (specifically the first and second image), different types of tissue within the tissue area may be clearly distinguished from one another on the basis of the detected light from different spectral ranges (specifically from the first and second spectral range) in conjunction with the visual highlighting in the superimposed image, thus resulting in the advantages already mentioned above.

The method may contain further steps and/or may be refined in accordance with the features already mentioned in conjunction with the imaging device.

The medical imaging device according to the present approach is particularly well-suited for use for examining a middle-ear tissue area by means of a method according to the invention for providing image-based support for a medical intervention.

In the case of this use, it is possible to conclude, by means of the highlight regions of the superimposed image, whether and where the middle-ear tissue area comprises defectively altered epithelial tissue, in particular cholesteatoma tissue. In particular, with this use, it is possible to benefit from the different reflection and absorption properties of cholesteatoma tissue and bone tissue already mentioned above. For example, on the basis of the visual highlighting, it is possible to check whether the cholesteatoma tissue has been fully removed during a surgical intervention or whether remnants of the cholesteatoma tissue still remain, which may then be identified again and removed.

BRIEF DESCRIPTION OF THE FIGURES

Embodiments of the present approach will be explained hereinafter with reference to FIG. 1 to FIG. 5. The figures show, schematically:

FIG. 2b part of the medical imaging device according to FIG. 2a,

DETAILED DESCRIPTION

Figure 1:
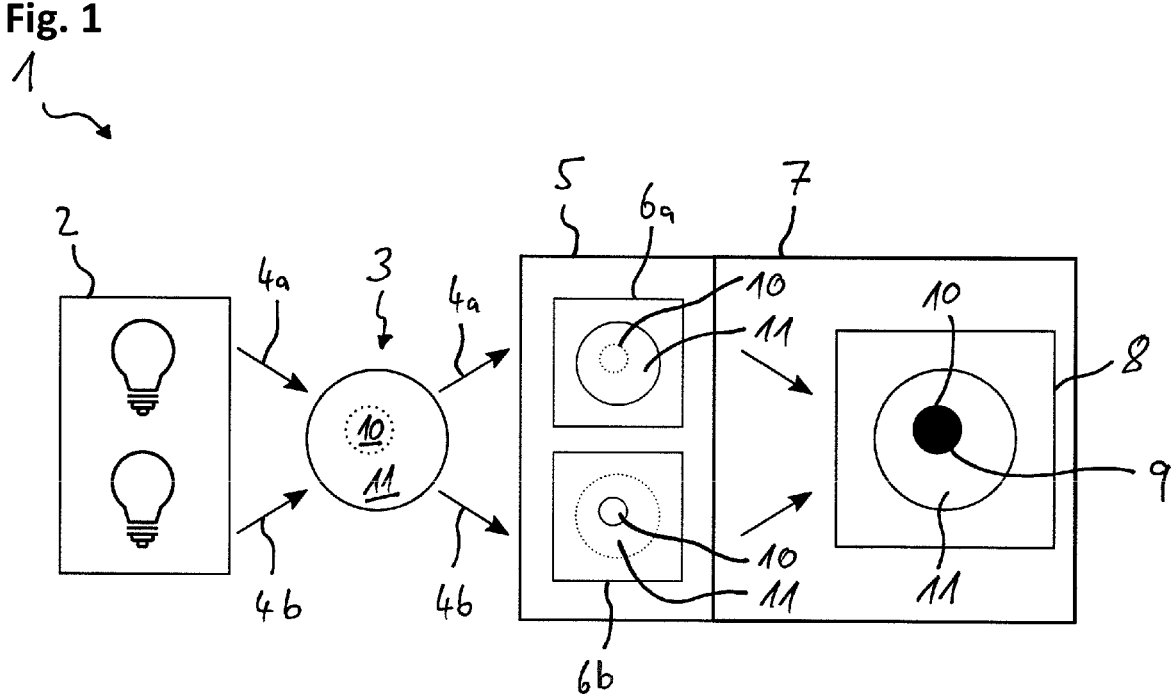
FIG. 1 a basic sketch of the functioning of a medical imaging device.

Recurrent and similar features in different embodiments are provided in the drawings with identical or similar alphanumerical reference signs.

The medical imaging device 1 sketched in FIG. 1 comprises an illumination unit 2, configured to illuminate a tissue area 3 with light 4a from a first spectral range, comprising a range of visible wavelengths, and with light 4b from a second spectral range, which is different from the first spectral range, an imaging unit 5, configured to detect light 4a from the first spectral range and to generate a first image 6a of the tissue area 3 on the basis of the detected light 4a from the first spectral range and furthermore configured to detect light 4b from the second spectral range and to generate a second image 6b of the tissue area 3 on the basis of the detected light 4b from the second spectral range, a superposition unit 7, configured to generate a superimposed image 8 on the basis of the first and second image 6a and 6b in such a way that, in the superimposed image, on the basis of a visual highlighting 9, it is possible to identify whether and where the tissue area 3 comprises highlight regions 10 which are characterized by an increased emission of light 4b from the second spectral range in comparison to other regions 11 of the tissue area 3.

In the superimposed image 8, both the other regions 11 and—on the basis of the visual highlighting 9—the highlight regions 10 are clearly visible. A distinction between different types of tissue in the tissue area 3 in comparison to the first image 6a and the second image 6b is thus simplified, since in the second image 6b the highlight regions 10, but not the other regions 11, are clearly visible, but by contrast a good overview of the tissue area 3 is provided in the first image 6a, however the highlight regions 10 therein are not clearly distinguishable from the other regions 11.

Figure 2A:
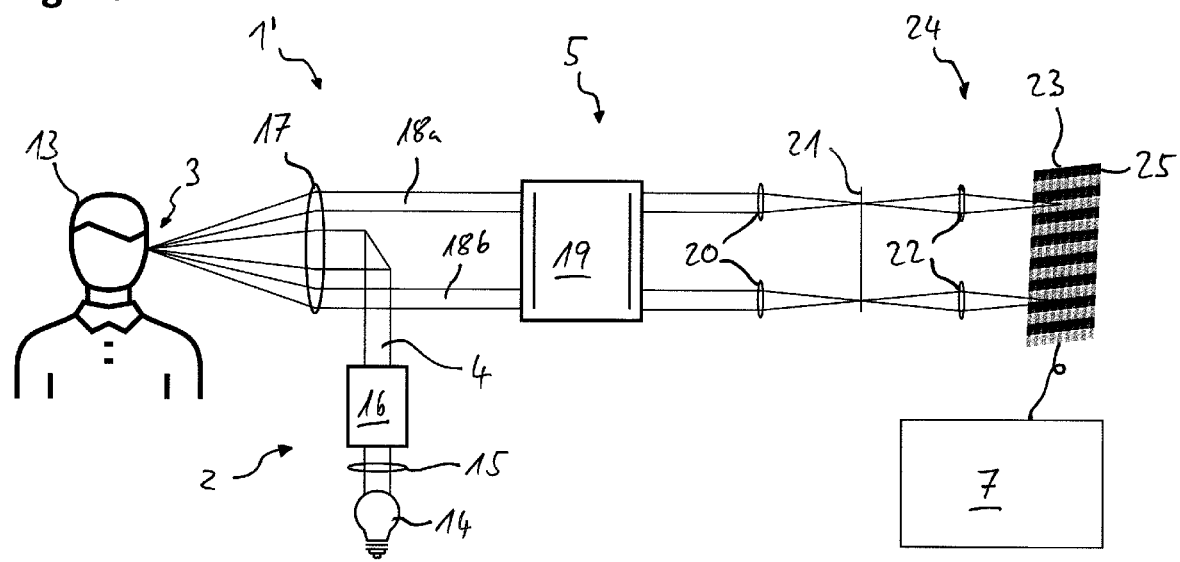
FIG. 2a a beam path of an exemplary medical imaging device.

The medical imaging device 1' shown in FIG. 2a is designed as an ENT microscope, which also serves as a surgical microscope. The imaging device 1' is thus particularly suitable for the examination of a tissue area 3 in the middle ear of a patient 13.

A illumination unit 2 of the imaging device 1' comprises a broadband light source 14 (for example a halogen-metal halide lamp, a xenon light source, a broadband LED light source, or a broadband LED light source unit, comprising a plurality of narrow-band LED light sources) for illuminating the tissue area 3 with light 4 from a first and second spectral range, the first spectral range corresponding to a wavelength interval of approximately 400 nm to 700 nm (light generated by the broadband light source 14 outside this wavelength interval may be suppressed by means of a bandpass filter).

The second spectral range, in this example, corresponds to a wavelength interval of from 400 nm to 450 nm. A separate light source is not necessary for the second spectral range, since the second spectral range is contained in the first spectral range, whereby the illumination unit 2 is configured to simultaneously illuminate the tissue area 3 with light 4 from the first and second spectral range.

The light 4 emitted by the broadband light source 14 may be coupled into an objective 17 by means of a collector lens 15 and a condenser 16 in order to illuminate the tissue area 3.

By means of the objective 17, light emitted (in particular reflected and scattered) by the tissue area 3 is detected. The light detected by means of the objective 17 is fed to an imaging unit 5 and is divided into two beam paths 18a and 18b, which correspond to the left and right component of a stereo image for three-dimensional imaging of the tissue area 3. Alternatively, one of the beam paths 18a and 18b may be omitted, and the tissue area 3 may be imaged two-dimensionally.

An enlargement of the imaging may be adjusted by means of a zoom unit 19 introduced into the beam paths 18a and 18b. By means of a tube lens 20, the tissue area 3 is imaged in an intermediate image plane 21, and, from there, is imaged by means of imaging lenses 22 into an image plane corresponding to the surface of an image sensor 23. Here, the beam paths 18a and 18b correspond to two separate regions of the image sensor 23, which correspond to the left and right components of the stereo image. The imaging lenses 22 and the image sensor 23 are part of a detection unit 24.

The image sensor 23 has a plurality of similar pixel groups 25, which are arranged in a plurality of rows of a plurality of pixel groups 25. One of the pixel groups 25 has been shown on an enlarged scale in FIG. 2b. The pixel group 25 comprises nine pixels 26a-26i, which are arranged in three rows of three pixels each (26a-26c, 26d-26f, 26g-26i).

A bandpass filter (not shown) is arranged on each of the pixels, and in this example the bandpass filters of pixels 26a-26c correspond to three sub-ranges of the second spectral range, the bandpass filters of pixels 26d-26i correspond to sub-ranges of the first spectral range lying outside the second spectral range, and therefore the pixels 26a-26i are configured together for the simultaneous and spatially separate detection of light from the first and second spectral range. The pixel groups may comprise a different number of pixels. The first and second spectral range may be divided across the various pixels in a different way by means of different combinations of bandpass filters.

The tissue area 3 is spatially resolvable by the pixel groups 25, and the detected light is spectrally resolvable by the individual pixels 26a-26i of each pixel group, and, in particular, may be combined in order to generate a first image, corresponding to light from the second spectral range detected by means of the pixels 26a-26c, and a second image, corresponding to light from the first spectral range detected by means of the pixels 26a-26i.

The image sensor 23 is connected to a superposition unit 7 (shown in FIG. 2a), in this example an image processing unit, which is configured to process the first image (in the form of a first pixel dataset) and the second image (in the form of a second pixel dataset). In particular, the superposition unit is configured to generate a superimposed image (in the form of a third pixel dataset) on the basis of the first and second image.

The imaging device 1' is configured to repeatedly generate the first image, the second image and the superimposed image by detecting a series of images, comprising alternating first and second images, by means of the image sensor 23 and by processing the series of images to generate a series of superimposed images. The detection unit 24, by the provision of a correspondingly high image repetition rate of the image sensor 23, is configured for the repeated detection of images with a repetition frequency of at least 60 Hz. The superposition unit 7, by use of a processing unit with sufficient processing power, is configured to generate the third pixel dataset with a latency of less than 50 ms.

The superposition unit 7 comprises a display unit for displaying the superimposed image with the visual highlighting.

The image processing unit furthermore comprises a user interaction unit, by means of which a user may choose one or more image processing options for the generation of the superimposed image and one or more display options for the display of the superimposed image. Alternatively, an image processing option and/or a display option may also be fixed, or other image processing options and/or display options may be selectable as described hereinafter.

The superposition unit 7 is configured to generate a highlight image according to the selected image processing option, which highlight image comprises the visual highlighting.

The following are selectable by means of the user interaction unit as image processing options for generation of the highlight image: generation of the highlight image by means of a threshold value for the second image, generation of the highlight image by means of a segmentation of the second image by means of edge detection, generation of the highlight image by means of a segmentation of the second image by means of a region detection (for example by means of a region-growing algorithm), generation of the highlight image by means of a color space transformation (for example by replacement of wavelengths which are not clearly visible by display colors that are clearly visible), generation of the highlight image with use of a principal component analysis (PCA) and/or an independent component analysis (ICA).

Other image processing options may also be selectable alternatively or additionally, for example use of a feature extraction and/or an object classification and/or a machine learning algorithm and/or a neural network.

The superposition unit 7 is configured to generate the superimposed image by superimposing the first image with the highlight image and to display the superimposed image in accordance with the selected display options. Alternatively, the superimposed image may also be generatable by replacing regions of the first image by the highlight image or by corresponding regions of the highlight image.

The following are selectable by means of the user interaction unit as display options: display of the visual highlighting as a color-based delimitation of the highlight regions (for example by means of a selectable highlight color or a selectable color assignment table, wherein the color assignment table for example may assign different highlight colors to different values of a quantitative feature, for example of a quotient of pixel values of the second and first image), display of the visual highlighting as an edging of the highlight regions, marking of an absence of highlight regions by means of a symbol introduced into the superimposed image, superposition of contour lines, which correspond to different values of a quantitative feature.

The display unit configured to display the superimposed image with the visual highlighting may be, for example, a conventional computer display, configured to display the superimposed image as a two-dimensional display image, or a 3D display, configured to display the superimposed image as a stereo image and/or as an AR display, for example a computer display usable in conjunction with 3D glasses, or 3D glasses with built-in displays for both eyes of the user.

In a further embodiment modified in comparison to the imaging device 1' shown in FIG. 2a only in respect of the detection unit 24 and/or the superposition unit 7, the imaging device (not shown) has two eyepieces. The eyepieces may be digital eyepieces (i.e. eyepieces with displays for displaying the above-described digital superimposed image) or optical eyepieces.

Optical eyepieces may replace the image sensor 23 in FIG. 2a and may be configured to view the superimposed image in the form of an optical image. In this example, the superposition unit is configured to generate the superimposed image by alternately displaying and hiding the first and second image, for example by alternately illuminating the tissue area 3 with light of the first and second spectral range, the frequency of the alternation being at least 30 Hz. The superimposed image is then created on the basis of the perception of the viewer, who perceives the rapidly alternating first and second images not as individual images, but as a superimposed image, with the visual highlighting being created purely optically since the second image basically shows the highlight regions. In the case of this optical superposition, in order for the highlight regions in the second image to appear clear and the first image to not be too bright in comparison to the second image, the first image may be softenable by means of a gray filter and/or an illumination level of the illumination with light from the first and/or second spectral range may be suitably adjustable.

Figure 3:
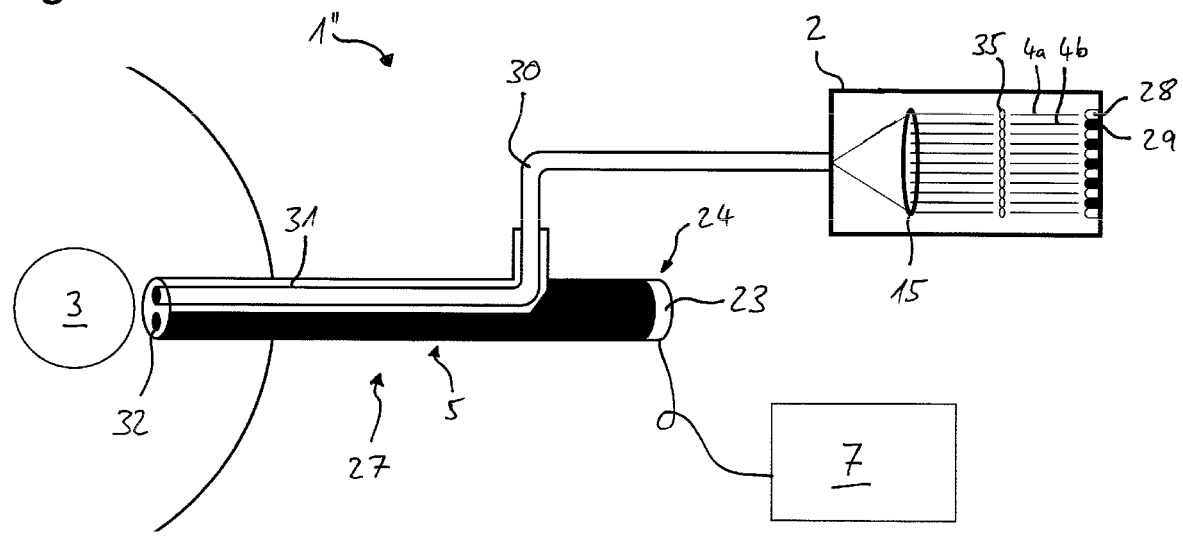
FIG. 3 an arrangement sketch of a further example of a medical imaging device.

The medical imaging device 1" shown in FIG. 3 comprises an endoscope 27, which is suitable for use in different diagnostic and/or surgical interventions for examining a tissue area 3.

The imaging device 1" comprises an illumination unit 2, which comprises a plurality of first LEDs 28, configured to emit light 4a from a first spectral range, and a plurality of LEDs 29, configured to emit light 4b from a second spectral range.

The first spectral range, in this example, corresponds to a wavelength interval of from approximately 400 nm to 700 nm. The second spectral range consists of two sub-ranges which correspond to the wavelength intervals of from 480 nm to 500 nm and from 620 nm to 660 nm. Light generated by the LEDs 28, 29 outside the wavelength intervals may be suppressed, as applicable, by means of bandpass filters.

By means of this selection of the first and second spectral range, the imaging device is well suited, for example, for the examination of nerve tissue, in particular for distinguishing between parotid and/or nerve tissue and surrounding tissue, since parotid and nerve tissue have an increased reflection and reduced absorption at wavelengths of approximately 490 nm and approximately 640 nm in comparison to surrounding tissue.

The light 4a, 4b emitted by the LEDs 28, 29 may be coupled into a light channel 31 of the endoscope 27 by means of a plurality of lenslets 35, a collector lens 15 and an optical waveguide 30 in order to illuminate the tissue area 3.

Light 4a, 4b from the first and second spectral range emitted (in particular reflected and scattered) by the tissue area 3 is detected by means of an imaging unit 5, which comprises a plurality of lenses arranged in an optical channel 32 of the endoscope 27, whereby the tissue area 3 is imaged onto an image sensor 23 of a detection unit 24 arranged at an end of the endoscope 27, said image sensor 23 being a monochrome CCD or CMOS sensor.

The illumination unit 2 is configured for the sequential illumination of the tissue area 3 with light 4a, 4b from the first and second spectral range. To this end, the first and second LEDs 28, 29 are switchable on and off in alternation. Alternatively, the illumination unit may have a broadband light source and a switchable filter unit for sequential illumination of the tissue area 3.

The imaging unit 5 is configured for sequential generation of a first image, on the basis of the detected light 4a from the first spectral range, and of a second image, on the basis of the detected light 4b from the second spectral range. To this end, the alternate switching on and off of the first and second LEDs 28 is synchronized with a detection of a series of images by means of the image sensor 23, so that the first and second image within the series of images alternate.

The image sensor 23 is connected to a superposition unit 7, in this example an image processing unit, which is configured to process the first image (in the form of a first pixel dataset) and the second image (in the form of a second pixel dataset). In particular, the superposition unit is configured to generate a superimposed image on the basis of the first and second image as described in greater detail above in conjunction with the imaging device 1', with the difference that the first image, the second image, and a superimposed image in this example each comprise only one component, that is to say are two-dimensional images and not stereo images. The imaging device 1" of this example, however, may also be configured alternatively for the generation of stereo images.

The image sensor 23 may also be an RGB sensor, that is to say an image sensor with a plurality of pixel groups which each comprise a pixel for detecting a red component, a pixel for detecting a green component and a pixel for detecting a blue component of the visible light, with one of the components, in particular the blue component, possibly corresponding to the second spectral range. The image sensor may also be a snapshot sensor (as described above) or another type of image sensor. For example, the illumination units, imaging units and/or detection units of the imaging devices 1' and 1" may also be combined with one another in different ways, and, accordingly, a sequential and/or simultaneous illumination with light from the first and second spectral range may be combined with a sequential and/or simultaneous and/or spatially separate and/or temporally separate detection of light from the first and second spectral range.

Figure 4:
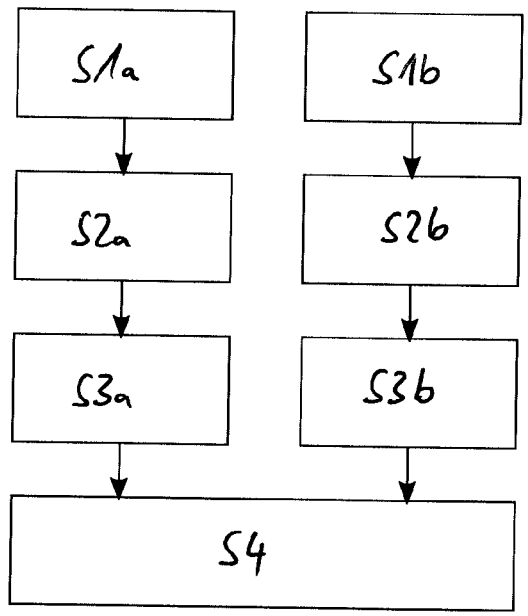
FIG. 4 a flow diagram of a method for providing image-based support for a medical intervention, FIG. 5 spectral absorption curves of different types of tissue.

An exemplary method for providing image-based support for a medical intervention will be described hereinafter with reference to FIG. 4.

First method steps S1a and S1b comprise an illumination of a tissue area with light from a first spectral range, comprising a range of visible wavelengths (step S1a), and with light from a second spectral range, which is different from the first spectral range (step S1b). Steps S1a and S1b may be performed simultaneously or sequentially.

Second method steps S2a and S2b, which likewise may be performed simultaneously or sequentially, comprise a detection of light from the first spectral range (step S2a) and from the second spectral range (S2b).

Third method steps S3a and S3b comprise a generation of a first image of the tissue area on the basis of the detected light from the first spectral range (step S3a) and of a second image of the tissue area on the basis of the detected light from the second spectral range (step S3b). Steps S3a and S3b, again, may be performed simultaneously or sequentially.

A fourth method step S4 comprises a generation of a superimposed image from the first and second image in such a way that, in the superimposed image, on the basis of a visual highlighting, it is possible to identify whether and where the tissue area comprises highlight regions which are characterized by an increased emission of light from the second spectral range in comparison to other regions of the tissue area.

The method may contain further steps and/or may be refined in accordance with the features already described in conjunction with the medical imaging devices 1, 1',1" and in the claims and the rest of the description.

Figure 2B:

As already indicated in conjunction with the imaging device 1' according to FIG. 2a/FIG. 2B, such an imaging device may be used in the described method in order to examine a middle-ear tissue area, and, by means of the highlight regions of the superimposed image, it is possible to conclude whether and where the middle-ear tissue area comprises defectively altered epithelial tissue, in particular cholesteatoma tissue.

Figure 5:
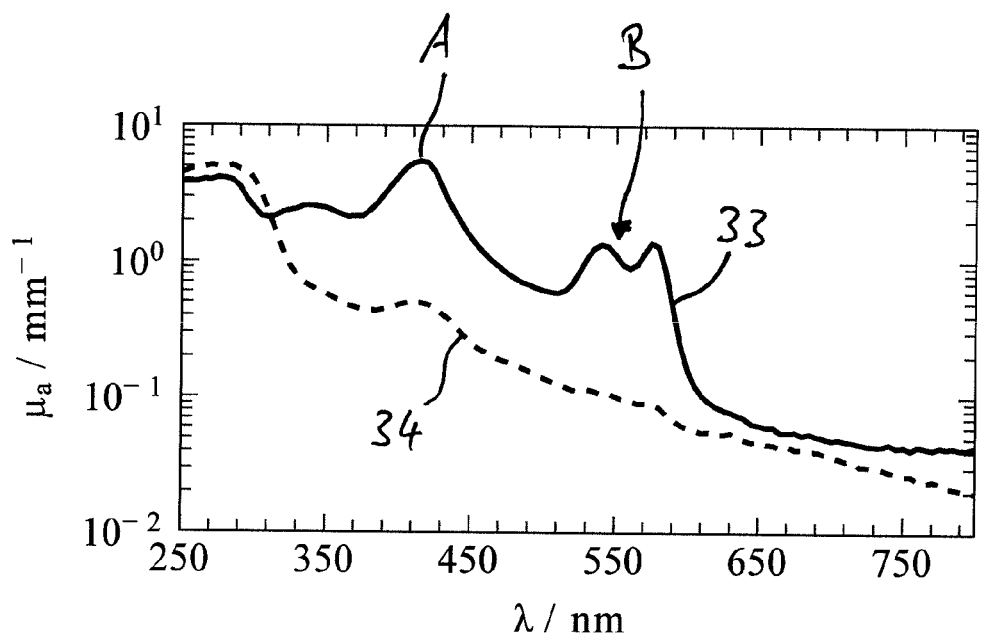

This use is based on the knowledge of measured spectral properties of cholesteatoma tissue and bone tissue which are shown in FIG. 5.

The curve 33 (solid line) shows an absorption coefficient $p_a$ of bone tissue of the middle ear (averaged over a number of samples) determined by means of a measurement using a double-beam spectrometer in units of $mm^{-1}$ as a function of a light wavelength $\lambda$ in units of nm. The curve 34 (dashed line) shows an absorption coefficient $p_a$ of cholesteatoma tissue of the middle ear (averaged over a number of samples) determined by means of a measurement using a double-beam spectrometer in units of $mm^{-1}$ as a function of a light wavelength $\lambda$ in units of nm.

On the basis of the curves 33 and 34 it is clear that cholesteatoma tissue has an increased reflection and reduced absorption of, in particular, near-ultraviolet light, blue light and blue-green light in comparison to surrounding bone tissue in the middle ear. Both curves are practically congruent below approximately 310 nm. The wavelength range of increased absorption by cholesteatoma tissue starts above approximately 310 nm and extends on the whole to approximately 600 nm, although it should be noted that the local absorption maxima A (around 400 nm) and B (double maximum around 550 nm) occur on account of spectral properties in the blood remaining in the bone tissue samples, and therefore the spectral differences between cholesteatoma tissue and the actual bone tissue approach one another again already below 600 nm with increasing wavelength. Above 600 nm, the two curves are again practically congruent.

Therefore, a selection of the second spectral range so that it corresponds approximately to the wavelength interval of from 370 nm to 480 nm or one or more sub-intervals thereof is particularly well suited for a distinction between the two types of tissue (cholesteatoma tissue and bone tissue), since in this range the difference between the absorption of the two types of tissue is almost one order of magnitude. For the specified use, a selection of the first and second spectral range as for the medical imaging device 1' (see description of FIG. 2a and FIG. 2b) is thus very suitable, and such a selection of the spectral ranges may also be provided for the imaging device 1" or any other embodiment of the imaging device according to the invention.

List of Reference Signs
1, 1',1" imaging device
2 illumination unit
3 tissue area
4, 4a, 4b light
5 imaging unit
6a first image
6b second image
7 superposition unit
8 superimposed image
9 visual highlighting
10 highlight region
11 other region
13 patient
14 broadband light source
15 collector lens
16 condenser
17 objective
18a, 18b beam paths
19 zoom unit
20 tube lens
21 intermediate image plane
22 imaging lens
23 image sensor
24 detection unit
25 pixel group
26a-26i pixels
27 endoscope
28 first LED
29 second LED
30 light guide
31 light channel
32 optical channel
33 absorption coefficient of bone tissue
34 absorption coefficient of cholesteatoma tissue
35 lenslets
A, B absorption maxima
S1a-S4 method steps

The invention claimed is:

1. A medical imaging device, comprising:
an illumination unit configured to illuminate a middle-ear tissue area with light from a first spectral range, comprising a range of visible wavelengths, and with light from a second spectral range, which is different from the first spectral range;
an imaging unit configured to detect light from the first spectral range and to generate a first image of the middle-ear tissue area based on the detected light from the first spectral range, wherein the first spectral range includes at least one subrange of visible wavelengths greater than 450 nm, and wherein the imaging unit is furthermore configured to detect light from the second spectral range and to generate a second image of the middle-ear tissue area based on the detected light from the second spectral range, wherein the second spectral range includes at least one subrange of wavelengths between 350 nm and 500 nm, and wherein the second spectral range omits at least one subrange of wavelengths smaller than 380 nm; and
a superposition unit configured to generate a superimposed image using on the first and second image, wherein the superimposed image, on the basis of includes a visual highlighting, to identify whether and where the middle-ear tissue area comprises one or more highlighted regions including cholesteatoma tissue, wherein the one or more highlighted regions including cholesteatoma tissue include an increased emission of light from the second spectral range in comparison to other regions of the middle-ear tissue area including bone tissue to differentiate the cholesteatoma tissue from the bone tissue.

2. The medical imaging device according to claim 1, wherein the second spectral range omits at least one subrange of wavelengths greater than 450 nm.

3. The medical imaging device according to claim 1, wherein the illumination unit is configured for a sequential illumination of the middle-ear tissue area with light from the first and second spectral range, and/or wherein the imaging unit is configured for a sequential generation of the first and second image.

4. The medical imaging device according to claim 1, wherein the illumination unit is configured for a simultaneous illumination of the middle-ear tissue area with light from the first and second spectral range, and/or wherein the imaging unit is configured for a simultaneous generation of the first and second image, wherein the first and second image are spatially separated by means of at least one optical filter.

5. The medical imaging device according to claim 1, wherein the superposition unit is configured to generate the superimposed image by at least one of alternate generation, display, hiding, or refreshing of the first and second image, wherein a frequency of at least one of the alternation between the first and second image, the refreshing of the first or second image, generation of the first or second image, display of the first or second image, hiding of the first or second image is at least 30 Hz.

6. The medical imaging device according to claim 1, wherein the medical imaging device is or comprises an ENT microscope, a surgical microscope, or an endoscope.

7. The medical imaging device according to claim 1, furthermore comprising:
a detection unit configured to detect a first pixel dataset, corresponding to the first image generated by the imaging unit, and a second pixel dataset, corresponding to the second image generated by the imaging unit, wherein the detection unit includes at least one image sensor configured for spatially resolved detection of at least one of the first pixel dataset or the second pixel dataset, and wherein the superposition unit is or comprises an image processing unit which is configured to generate a third pixel dataset, corresponding to the superimposed image, based the first and second pixel dataset.

8. The medical imaging device according to claim 7, wherein the detection unit is configured for a repeated detection of images with a repetition frequency of at least 30 Hz, preferably at least 60 Hz, and/or wherein the image processing unit is configured to generate the third pixel dataset with a latency of less than 100 ms.

9. The medical imaging device according to claim 7, wherein the detection unit comprises an image sensor with a plurality of pixel groups and each of the pixel groups comprises at least one first pixel, configured to detect light from the first spectral range, and at least one second pixel, configured to detect light from the second spectral range.

10. The medical imaging device according to claim 9, wherein the pixel groups are arranged, in a coplanar manner, in multiple rows of multiple pixel groups per row, in particular on a joint sensor chip.

11. The medical imaging device according to claim 7, wherein the image processing unit is configured to generate the visual highlighting by at least one of: means of a threshold value for the second image, means of a segmentation of the second image, means of a color space transformation, a feature extraction, an object classification, a pattern recognition, a principal component analysis, or an independent component analysis.

12. The medical imaging device according to claim 1, wherein the first spectral range omits at least one subrange of the second spectral range.

13. A method for providing image-based support for a medical intervention comprising the following steps:
illuminating a middle-ear tissue area with light from a first spectral range, comprising a range of visible wavelengths, and with light from a second spectral range, which is different from the first spectral range wherein the first spectral range includes at least one subrange of visible wavelengths greater than 450 nm, wherein the second spectral range includes at least one subrange of wavelengths between 350 nm and 500 nm, and wherein the second spectral range omits at least one subrange of wavelengths smaller than 380 nm;
detecting light from the first spectral range and from the second spectral range;
generating a first image of the middle-ear tissue area based on the detected light from the first spectral range and a second image of the middle-ear tissue area based on the detected light from the second spectral range;
generating a superimposed image from the first and second image in such a way that, in the superimposed image, on the basis of a visual highlighting, it is possible to identify whether and where the middle-ear tissue area comprises highlight regions which are characterized by an increased emission of light from the second spectral range in comparison to other regions of the tissue area, and
examining the middle-ear tissue to differentiate cholesteatoma tissue from bone tissue.

14. The method according to claim 13, wherein the first spectral range omits at least one subrange of the second spectral range.

* * * * *